(12) United States Patent
Lichten

(10) Patent No.: US 6,488,649 B1
(45) Date of Patent: Dec. 3, 2002

(54) IMPLANT DEVICE

(76) Inventor: Edward M. Lichten, 695 Rudgate, Bloomfield, MI (US) 48304

( * ) Notice: Subject to any disclaimer, the term of this patent is extended or adjusted under 35 U.S.C. 154(b) by 0 days.

(21) Appl. No.: 09/448,340

(22) Filed: Nov. 23, 1999

Related U.S. Application Data

(60) Provisional application No. 60/109,684, filed on Nov. 24, 1998.

(51) Int. Cl.$^7$ ............................................. A61M 31/00
(52) U.S. Cl. .......................... 604/64; 606/185; 221/303
(58) Field of Search ............................. 604/60, 62, 64, 604/71, 59, 57, 165.02, 164.01, 15, 16, 18, 164.12, 235; 606/184, 185, 187, 188; 222/145.1, 386; 221/113, 115, 303, 307, 308

(56) References Cited

U.S. PATENT DOCUMENTS

| | | | |
|---|---|---|---|
| 405,598 A | * | 6/1889 | Raymond .................... 221/250 |
| 2,269,963 A | | 1/1942 | Wappler |
| 2,513,014 A | | 6/1950 | Fields |
| 2,718,299 A | | 9/1955 | Atwater et al. |
| 2,761,446 A | | 9/1956 | Reed |
| 2,885,116 A | | 5/1959 | Tregilgas |
| 3,921,632 A | | 11/1975 | Bardani |
| 4,147,164 A | * | 4/1979 | Behney ........................ 604/60 |
| 4,154,239 A | | 5/1979 | Turley |
| 4,244,944 A | | 1/1981 | Wilkinson |
| 4,531,938 A | * | 7/1985 | Kaye et al. .................. 206/528 |
| 4,597,753 A | | 7/1986 | Turley |
| 4,748,024 A | | 5/1988 | Leonard |
| 4,846,793 A | | 7/1989 | Leonard et al. |
| 4,863,736 A | | 9/1989 | Azain et al. |
| 4,982,734 A | | 1/1991 | Green et al. |
| 4,988,335 A | | 1/1991 | Prindle et al. |
| 4,994,028 A | | 2/1991 | Leonard et al. |
| 5,035,891 A | | 7/1991 | Runkel et al. |
| 5,110,595 A | | 5/1992 | Wang |
| 5,208,032 A | | 5/1993 | Scanes et al. |
| 5,279,554 A | | 1/1994 | Turley |
| 5,522,797 A | | 6/1996 | Grimm |
| 5,688,519 A | | 11/1997 | Leonard et al. |
| 5,830,130 A | * | 11/1998 | Janzen et al. .................. 604/15 |

* cited by examiner

Primary Examiner—Brian L. Casler
Assistant Examiner—Mark K Han
(74) Attorney, Agent, or Firm—Sonnenschein Nath & Rosenthal

(57) ABSTRACT

Disclosed is an implant device adapted to implant medicaments into the subcutaneous portion of the patient's tissue comprising a housing having a central chamber generally in which a pusher assembly maneuvers.

24 Claims, 3 Drawing Sheets

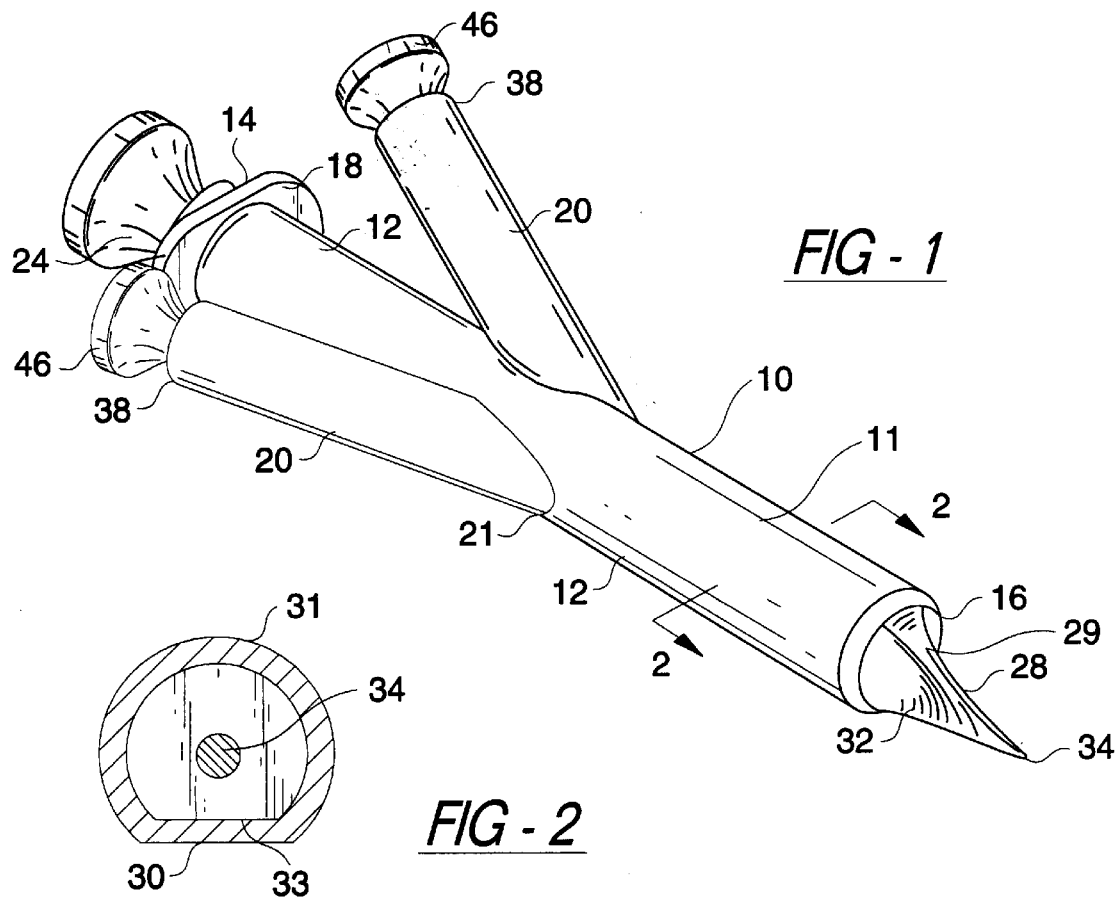
*FIG - 1*
*FIG - 2*
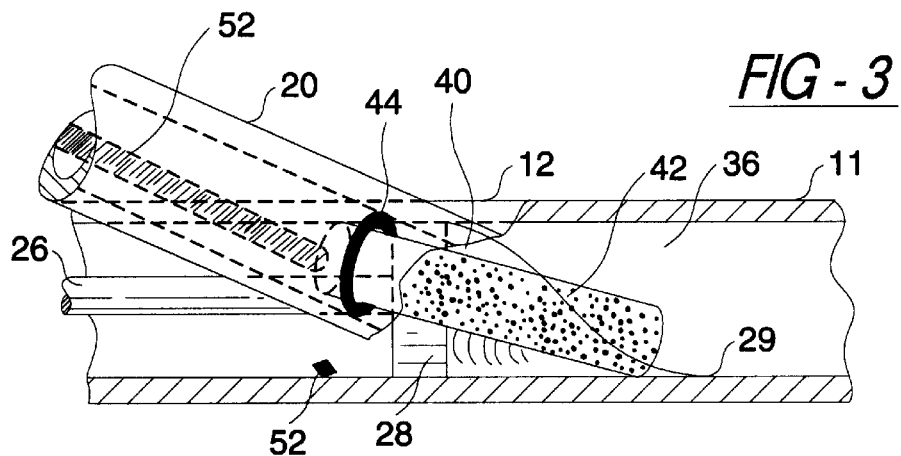
*FIG - 3*
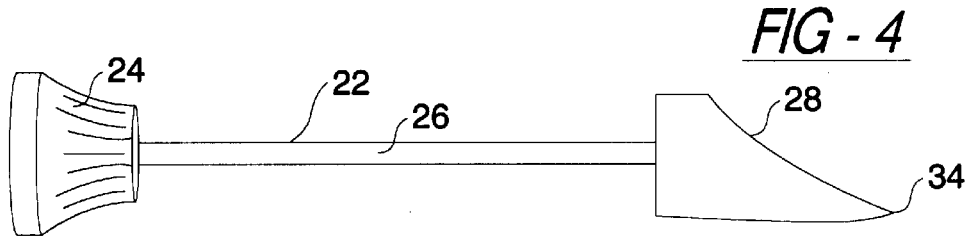
*FIG - 4*

IMPLANT DEVICE

This application claims the benefit of provisional application Ser. No. 60/109,684, filed Nov. 24, 1998.

FIELD OF THE INVENTION

The present invention relates to an improved device for administration of pellet medicaments into the subcutaneous tissue of a mammal, and in particular to a hand-held pre-loaded pellet implant device capable of sequentially implanting multiple pellets into the tissue.

BACKGROUND OF THE INVENTION

Subcutaneous insertion is one method of administration of solid medicaments into a patient. The medical use of subcutaneous implants has been successfully utilized in certain treatments where it is desirable to maintain within the body a slow, constant release and absorption of a drug over an extended period of time. Delivery of hormone treatments by medical implants has proven medically successful and economically advantageous over other drug administration methods. It has been found that other forms of pharmaceutical administration such as oral and parenteral administration cause a drug to dissipate rapidly by absorption into body tissues, and thereby require a patient to undergo repeated administration. Frequent administrations of a drug treatment can be both expensive and, in the case of parenteral administrations, sometimes quite painful. On the other hand, subcutaneous drug implants, where practicable, obviate the need for frequent administrations and thus solve the problems of expense and discomfort.

Prior art implant delivery devices, however, have not proven successful. Several prior art devices, such as the one disclosed in U.S. Pat. No. 5,522,797, teach the use of a pellet injector gun which operates by the use of a spring or other biasing mechanism. These prior art devices are commonly used by veterinary practitioners on animals. Additionally, there are prior art devices that disclose a hand-held, manual pellet injector, but these also suffer from several major defects. For example, the devices disclosed in U.S. Pat. Nos. 3,921,632 and 4,994,028, allow the pellets to be loaded in the implanting device only after the device has been inserted into the subcutaneous tissue. The design of these prior art devices make the pellets prone to being dropped, thereby causing the medicaments to lose sterility. Further, these devices allow only one pellet to be inserted at a time and are not easily manipulable even in single pellet loading. Moreover, these implanting devices depend on gravity to keep the pellets within the implanting devices prior to actual placement within a patient.

The implant device of the present invention constitutes a vast improvement over the prior art devices. Use of the present implanting device obviates the need to load the pellets after the placement of the implanting device because the pellets may be pre-loaded in a plurality of laterally extending loading chambers. Also, the presence of 'O' rings within the loading chambers and stoppers at the top of the loading chambers prevent the pellets from falling out and thus preserve pellet sterility. Moreover, a slidably movable plunger in a disposed central hollow chamber locks after being fully retracted thereby preventing reuse and possible blood contamination.

It is therefore an object of the present invention to provide a pellet implanting device having a plurality of pellet loading chambers.

It is also an object of the present invention to provide a pellet implanting device into which a plurality of pellets may be pre-loaded prior to incising a patient.

It is a further object of the present invention to provide a pellet implanting device that is capable of inserting a plurality of pellets at one incision.

It is yet another object of the present invention to provide a disposable pellet implanting device that is adapted for a single use.

It is still another object of the present invention to provide a pellet implanting device wherein pellets are held securely within the loading chambers.

These and other objects of the present invention will become increasingly more clear upon reading the following detailed description of the preferred embodiments in conjunction with the accompanying drawings.

SUMMARY OF THE INVENTION

According to the present invention, there is provided a device for the subcutaneous implanting of a pellet medicament into a mammal. The device includes a hollow central chamber through which a plunger assembly is slidably movable. The plunger assembly comprises a large head end in coaxial alignment with a stylet end. The stylet end of the plunger assembly is adapted to create a subcutaneous channel when inserted into and subsequently retracted from under the skin of a patient. In addition to being capable of forming a subcutaneous channel, the sides of the stylet end of the plunger are concave and slanted and therefore adapted to guide the pellets through the central chamber and into the subcutaneous channel after the stylet has been retracted into the central chamber. The interior of the central chamber further includes an automatic locking mechanism to lock the stylet end of the plunger assembly within the central chamber to prevent reuse.

Extending diagonally from the central chamber are a plurality of loading chambers into which medicinal pellets are pre-loaded. A finger hold is disposed proximate to a top end of the central chamber for single-handed hand use of the implant device. The interior of the loading chambers are in communication with the interior of the central chamber, but pellets are retained in the loading chambers by a plurality of 'O' rings disposed at the ends of the interior of the loading chambers. A manually insertable flexible prod is then utilized to push the pellets through the 'O' rings, then the central chamber, and then into one of the subcutaneous channels.

BRIEF DESCRIPTION OF THE DRAWINGS

FIG. 1 is a top perspective view of the implant device showing the stylet.

FIG. 2 is a cross-section view taken along line 2—2 in FIG. 1.

FIG. 3 is a partial cross-section view of the hollow central chamber illustrating the position of the stylet when locked within the central chamber.

FIG. 4 is a fragmentary side plan view of the plunger assembly.

DETAILED DESCRIPTION OF PREFERRED EMBODIMENTS

Figure 5:
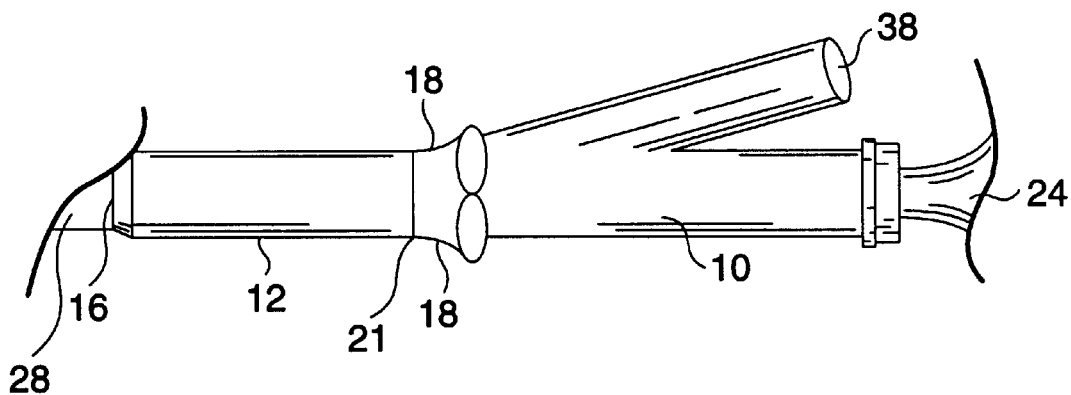
FIG. 5 is a side elevation view of the implant device with a partial cross section view of the stylet partially exposed.

Referring to FIGS. 1 and 2, the implant device 10 includes housing 11 having a central longitudinal hollow chamber 12 formed of plastic by means of injection molding or other similarly suitable process. In the preferred embodiment, the central chamber 12 is opaque or otherwise clear to allow one to visualize the pellets in the central chamber 12. Also in the preferred embodiment, the exterior surface of the central chamber 12 may be smooth, or alternatively, the central chamber 12 may have either a ridged or a spiraled texture. In the preferred embodiment the central chamber 12 is substantially round 31 and further includes a flat underside 30.

Figure 6:
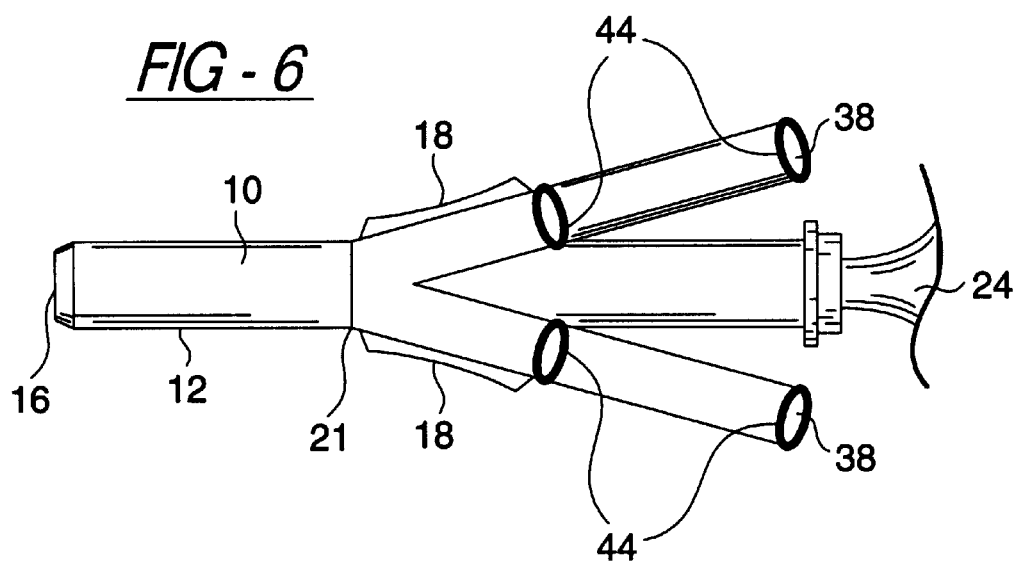
FIG. 6 is a top plan view partially in section showing the 'O' rings disposed within the loading chambers and an alternative finger hold at the junction where the loading chambers contact the central chamber.

The central chamber 12 comprises a top end 14 and a bottom end 16. As shown in FIG. 1, integrally disposed proximate to the top end 14 of the central chamber 12 is a finger hold 18 which, in the preferred embodiment, extends from the central chamber 12 as a horizontal flat platform. The finger hold 18 assists a user of the implant device 12 in controlling the amount of force to be applied to the plunger head 24 (as described below). Referring to FIGS. 5 and 6, finger hold 18 may alternatively be a concave hourglass member 21 disposed on a plurality of loading chambers 20, as described in greater detail below, proximate to a junction 21 where the loading chambers 20 join the central chamber 12. In yet another embodiment, the loading chambers 20 may be angled at least 60° from the axis of the central chamber 12 to accommodate finger positioning.

With reference to FIGS. 3 and 4, a slidably movable plunger assembly 22, comprising a plunger head 24 joined in coaxial alignment by a thin rod member 26 to a stylet end 28, is substantially disposed within the hollow portion 36 of central chamber 12. The plunger head 24 and the stylet end 28 are positioned respective to the top 14 and bottom ends 16 of the central chamber 12 wherein the plunger head 24 is disposed proximate to the exterior portion of the top end 14 of the central chamber 12. In the preferred embodiment, the plunger head 24 is a circular platform having a circumference that is adapted for gripping by a thumb and that is greater than that of the central chamber 12. The plunger head 24 may alternatively be comprised of any other shape suitable for gripping by a thumb. The stylet end 28 is adapted to penetrate a surface such as mammalian skin tissue. The general shape of the stylet end 28 necessarily corresponds to the shape of the hollow portion 36 of central chamber 12. Accordingly, as seen in FIG. 9, in the preferred embodiment the shape of the stylet end 28 is substantially round with a flat underside 33.

The plunger assembly 22 is longer than the length of the central chamber 12 and is slidably movable within the central chamber 12 whereby movement of the plunger assembly 22 is controlled by manual manipulation of the plunger head 24. Referring now to FIG. 3, the diameter of the stylet end 28 at its widest point is slightly less than the diameter of the interior 36 of the central chamber 12, which allows the plunger assembly 22 to frictionally move within the central chamber 12 when manual force is deliberately applied to the plunger head 24. Thus, a continuous and even amount of downward pressure is applied to the plunger head 24 when the plunger head 24 is in a raised position, causes the plunger assembly 22 to steadily slide downward until the plunger head 24 abuts the top 14 of the central chamber 12. At this point, the stylet end 28 is fully exposed from the bottom end 16 of the central chamber 12. When the plunger head 14 is raised from the abutting position from top 14 of the central chamber 12, the stylet end 28 is retracted within the central chamber 12.

Figure 9:
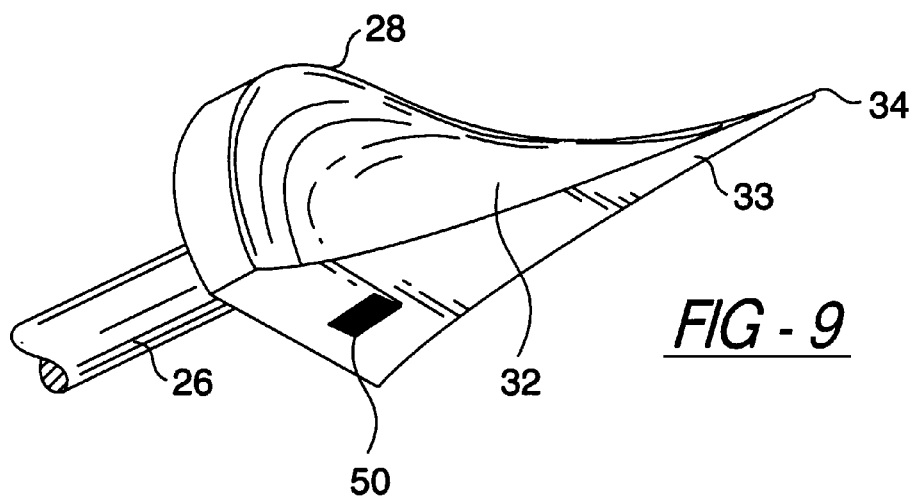
FIG. 9 is a detailed perspective view of the stylet end of the plunger.

As previously stated and as illustrated in FIGS. 2 and 9, in the preferred embodiment the stylet end 28 of the plunger assembly 22 is solid and substantially conically shaped wherein a bottom surface 33 of the stylet end 28 is flat and each side 32 of the stylet end 28 is concave up to a central rib 29 (FIG. 1), and slanted forward to a sharp pointed end 34. The slanting concave shape of the sides 32 of the stylet end 28 are more clearly illustrated in FIGS. 1 and 7. When the plunger head 24 is raised and the stylet end 28 is retracted from the skin of a patient, the slanting concave sides 32 of the stylet end 28 creates a distinct subcutaneous channel for pellet 42 placement, and further prevent the stylet 28 from coring skin tissue. In an alternative embodiment, the stylet end 28 may be of any known concave tip or bevel end which allows the stylet 28 to puncture skin tissue without coring any tissue or fluids.

Figure 7:
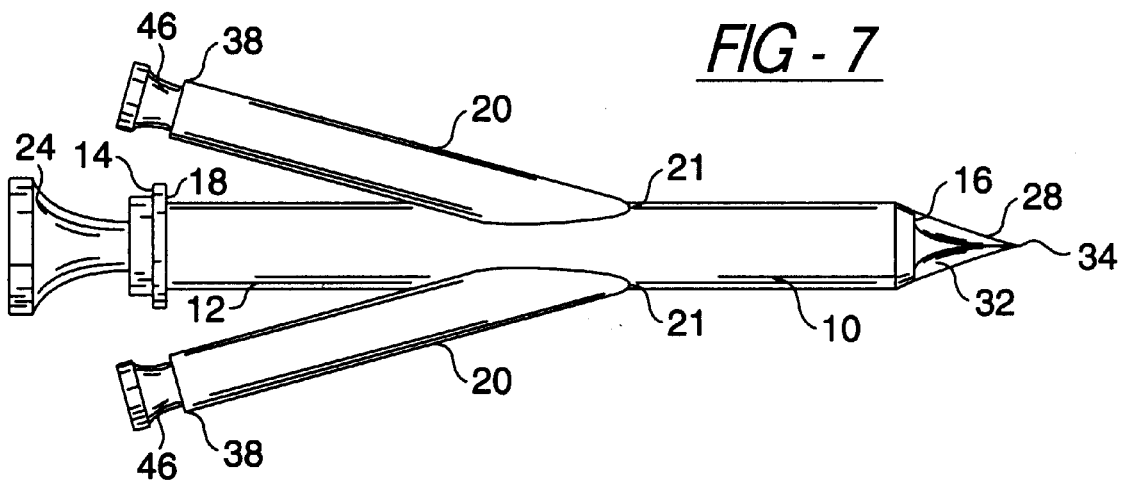
FIG. 7 is a top plan view of the implant device illustrating stoppers on the loading chambers and stylet fully exposed.
Figure 8:
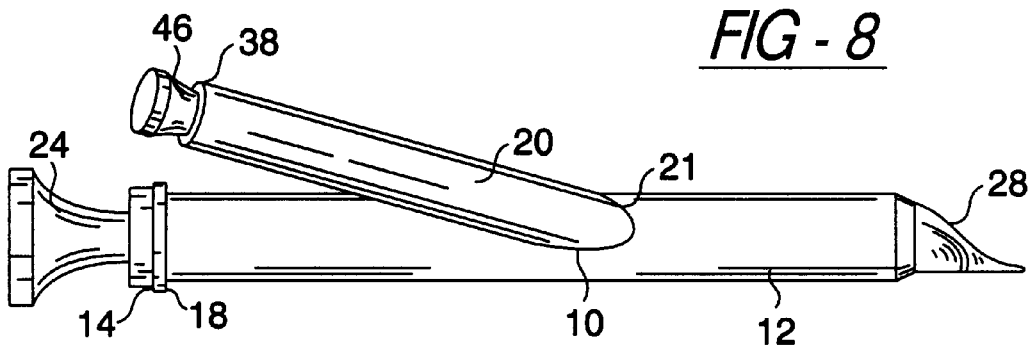
FIG. 8 is a side elevation view of the implant device.

Referring now to FIGS. 1, 7 and 8, a plurality of hollow pellet loading chambers 20 extend diagonally from the central chamber 12. The loading chambers 20 are formed of plastic by means of injection molding or other suitable process and the loading chambers 20 may be transparent to allow one to view the pellets 42 after loading. The loading chambers 20 include an inlet end 38 and an outlet end 40 (see FIG. 3). Pellets 42, such as the one shown in FIG. 3, are loaded into the loading chamber 20 through the inlet end 38, and the outlet end 40, which is in communication with the interior 36 of the central chamber 12, provides the egress of the pellets 42 into central chamber 12.

As shown in FIGS. 3 and 6, the interior surfaces of loading chambers 20 include a plurality of deformable 'O' rings 44 which have a diameter substantially the same as the diameter of the pellets 42. The 'O' rings 44 are disposed proximate to the inlet 38 and outlet ends 40 of the loading chambers 20 to prevent the pellets 42 from either prematurely falling into the central chamber 12, or falling out of the loading chamber 20, after the pellets 42 have been pre-loaded into the loading chamber 20. After loading the desired number of pellets 42 within the loading chambers 20, frictionally attachable stoppers 46 are fitted within each inlet end 38 of the loading chambers 20. The stoppers 46 protect foreign contaminants from entering into the loading chambers 20 during shipment and prior to use, and prevent pellets 42 from falling out from the inlet end 38 of the loading chamber 20. Alternatively, the stoppers 46 and the inlet end 38 of the loading chambers 20 may each be adapted for twistable attachment.

Referring again to FIG. 3, a locking mechanism 52 is disposed within the interior 36 of the central chamber 12 to permanently lock the plunger assembly 22 in a fully retracted position, thereby preventing the plunger assembly 22 from moving and the implant device 10 from re-use. In the preferred embodiment, the locking mechanism 52 comprises a resiliently deformable protuberance disposed on the interior 36 of the central chamber 12 proximate to the outlet ends 40 of the loading chambers 20. The locking mechanism 52 engages a corresponding recess 50 (shown in FIG. 9) in the underside 33 of the stylet end 28, thereby preventing the plunger assembly 22 from moving. Alternatively, a lure lock or other locking mechanism known in the art may be used in the present invention. Once locked, the plunger assembly 22 is no longer slidable and the entire implanting device 10 must be discarded.

When the plunger assembly 22 is engaged in the locked position, the slanting concave sides 32 of the stylet end 28 of the plunger assembly are positioned adjacent to the corresponding outlet ends 40 of the loading chambers 20. The slanting concave sides 32 of the stylet 28 function to guide the pellets 42 from the outlet ends 40 to the bottom end 16 of central chamber 12.

Figure 3A:
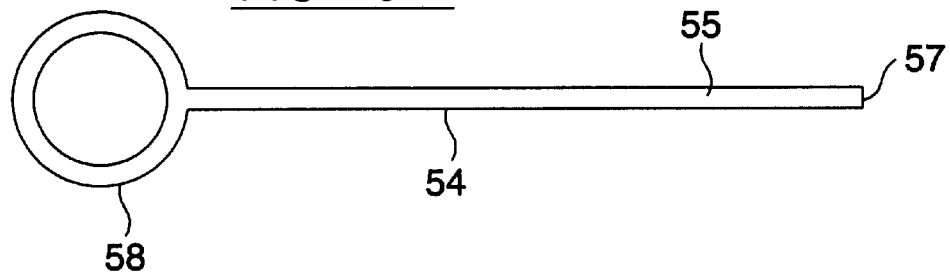
FIG. 3A is a side plan view of a flexible prod member.

With reference to FIGS. 3 and 3A, a flexible prod member 54 is used to sequentially advance the pellets from the loading chambers through the 'O' rings 44 disposed proximate to the outlet openings 40 into the central chamber 12. The flexible prod member 54 is molded from injected plastic or, alternatively, by another suitable means but may also be constructed from rubber or a flexible coated metal. In the preferred embodiment, the flexible prod member 54 comprises a linear, elongated member 55 having a flat end 57. The prod member 54 is inserted in one loading chamber and then the other to advance the pellets forward and out of the chambers 20. The flexible prod member 54 also includes a grippable loop or handle 58 disposed proximate to the center of the prod 54. The flexible prod member 54 should be of an appropriate length whereby it may extend from the inlet end 38 of the loading chambers 20, into the central chamber 12, and then into the subcutaneous channels in chamber 12 formed by the stylet 28.

To describe the implant procedure, the requisite number of pellets 42 are first manually loaded into the loading chambers 20 through the inlet ends 38 and past the deformable 'O' rings 44 disposed proximate to the inlet ends 38. After the desired number of pellets 42 are loaded into one or both of the loading chambers 20, the stoppers 46 are frictionally fitted onto the inlet end 38 of the loading chamber 20 to prevent contamination of the pellets 42. Also, the plunger head 24 is initially retracted so that the stylet 28 is disposed within the central chamber 12, however the plunger head 24 must not be fully retracted so that it does not engage the automatic locking mechanism 52. The implant device 10 may then be positioned for insertion of the pellets 42 into a patient.

The bottom end 16 of the implant device 10 is positioned on the epidermal surface and an amount of downward force is applied to the plunger head 24, thereby causing the stylet end 28 to pass through the bottom end 16 of the central chamber 12 and pierce the skin tissue and pass through to the subcutaneous layer. After reaching the desired depth, the stylet end 28 is retracted from the skin, the two concave surfaces 32 of the stylet 28 forming a subcutaenous channel in the skin of the patient. Simultaneous with the retraction of the plunger assembly 22, the central chamber 12 is advanced through the incised skin edge to maintain the integrity of the subcutaneous channel.

The stylet 28 is then fully retracted to engage the automatic locking mechanism 48 and prevent reuse of the implant device 10. Once the locking mechanism 48 is engaged, the stylet end 28 is properly positioned within chamber 36 so that the slanting concave sides 32 of the stylet 28 are adjacent to the outlet openings 40 of the loading chambers 20. Following full retraction of the stylet 28, the stoppers 46 covering the loading chambers 20 are removed so that the pellets 42 previously loaded in the loading chambers 20 are exposed.

The flexible prod 54 is used to sequentially push the pellets 42 through the deformable 'O' rings 44 at the outlet ends 40 of both loading chambers 20. The pellets 42 then contact the slanting concave sides 32 of the stylet end 28 which guide the pellets toward the bottom end 16 of the central chamber 12. The pellets 42 are then pushed through the bottom end 16 of the central chamber 12 and enter into the subcutaneous channel created by the stylet 28. After the loaded pellets 42 are inserted into the patient, more pellets 42 may be reloaded into the loading chambers whereby the flexible prod 54 is used to push the pellets 42 into the patient. After the desired number of pellets 42 are inserted into the patient, the implant device 10 may be disposed of in an appropriate sanitary container for sharp devices.

The implant device 10 may be inexpensively manufactured and may be supplied as presterilized, individually packaged devices where a single implant device is discarded after a single treatment.

While the specific invention has been described with particular emphasis on preferred embodiments, it will be obvious to those of ordinary skill in the art that variations in the preferred embodiment of the present invention may be used and that it is intended that the invention may be practiced otherwise than as specifically described herein. Accordingly, this invention includes all modifications encompassed within the spirit and scope of the invention as defined by the following claims.

What is claimed is:

1. A disposable, single-use hand-held implant device for introducing pellets into mammals, comprising:

a housing having a hollow central chamber;

a plunger assembly adapted for slidable movement within the central chamber, the plunger assembly comprising a plunger head end in coaxial alignment with a stylet end, the stylet end being adapted to puncture a surface;

a plurality of hollow pellet loading chambers in communication with the central chamber, the loading chambers being capable of receiving a plurality of pellets, and;

a manually insertable flexible prod for insertion into the loading chambers to advance the pellets from the pellet loading chambers and into the hollow central chamber;

wherein the hollow central chamber further includes a locking mechanism for permanently locking the stylet end of the plunger assembly within the hollow central chamber after the stylet end of the plunger assembly is fully retracted into the hollow central chamber.

2. The implant device according to claim 1 wherein the central chamber comprises a is top end and opposing bottom end.

3. The implant device according to claim 2 wherein a broad flat platform arm is mounted proximate to the top end of the central chamber.

4. The implant device according to claim 1 wherein the plunger assembly further comprises a plunger head end adaptable to be manually engaged, and a stylet end comprising a substantially conical pointed tip, the stylet end having a substantially flat underside and slanting concave sides for guiding an inserted pellet toward the bottom end of the central chamber, and a sharp end for penetrating a surface.

5. The implant device according to claim 1 wherein the loading chambers angularly adjoin the central chamber such that the interior of the loading chambers are in communication with the interior of the central chamber at substantially opposing sides of the central chamber.

6. The implant device according to claim 5 wherein a single loading chamber comprises an inlet for insertion of a pellet and an outlet in communication with the interior of the central chamber.

7. The implant device according to claim 6 wherein a plurality of deformable 'O' rings are disposed within the loading chambers to frictionally prevent a pellet from prematurely entering the central hollow chamber.

8. The implant device according to claim 6 wherein at least one deformable O ring is disposed at the inlet end of the loading chamber and at least one deformable O ring is disposed at the outlet end of the loading chamber.

9. The implant device according to claim 1 wherein a manually insertable removable stopper is fitted on the inlet ends of the loading chambers.

10. The implant device according to claim 1 wherein the flexible prod is comprised of an elongated member having a grippable end and being constructed from a tensile material selected from the group consisting of plastic, rubber, and coated flexible metal.

11. A device, comprising:
   a housing having a hollow central chamber, the housing having a longitudinal axis;
   a plunger assembly adapted to move within the central chamber, the plunger assembly being adapted to penetrate a surface;
   a plurality of hollow pellet loading chambers, each having a proximal and a distal end, the chambers being in communication with the central chamber, the loading chambers being configured to receive a plurality of pellets, and;
   the pellet loading chamber further includes a means for preventing the received pellets from prematurely exiting the pellet loading chamber;
   wherein the hollow central chamber further includes a locking mechanism for permanently locking a stylet end of the plunger assembly within the hollow central chamber after the stylet end of the plunger assembly is fully retracted in the hollow central chamber.

12. The device of claim 11, wherein the plurality of loading chambers connect to the central chamber at an angle to the housing longitudinal axis.

13. The device of claim 11, wherein the means for preventing the premature exit of pellets further includes a plurality of O-shaped rings disposed within the chamber.

14. The device of claim 13, wherein the O-shaped rings are disposed at the distal and proximal ends of the-loading chambers.

15. The device of claim 13, wherein the O-shaped rings are disposed at the proximal end of at least one of the loading chambers.

16. The device of claim 13, wherein the O-shaped rings are disposed at the distal end of at least one of the loading chambers.

17. The device of claim 11, wherein the plunger assembly further comprises a plunger head end adaptable to be manually engaged, and the stylet end comprising a substantially conical pointed tip, the stylet end having a substantially flat underside and slanting concave sides for guiding an inserted pellet toward the bottom end of the central chamber, and a sharp end for penetrating a surface.

18. A method for the subcutaneous insertion of pellet medicaments into a mammal using a pellet implant device comprising the steps of:

(a) pre-loading a pre-determined number of pellets into a plurality of pellet loading chambers of a pellet implant device;

(b) inserting a sharp stylet into mammalian skin tissue;

(c) simultaneously retracting the sharp stylet to create at least one subcutaneous channel and inserting the pellet implant device into the at least one subcutaneous channel;

(d) implanting the pre-loaded pellets from the pellet implant device into the at least one subcutaneous channel; and (e) completely removing the pellet implant device from the at least one subcutaneous channel.

19. The subcutaneous insertion method according to claim 18 whereby step (d) includes reloading the pellet loading chambers to allow for implanting of additional pellets.

20. The subcutaneous insertion method according to claim 18 hereby step (c) includes partially inserting the pellet implant device at a distance sufficient to maintain the at least one subcutaneous channel created by the retracted sharp stylet.

21. An implant device to introduce pellets into a patient, comprising:
   a housing having a hollow central chamber;
   a plunger assembly adapted for slidable movement within the central chamber, the plunger assembly comprising a plunger head end in coaxial alignment with a stylet end, the stylet end being adapted to penetrate a surface;
   a plurality of hollow pellet loading chambers in communication with the central chamber, the loading chambers being capable of receiving a plurality of pellets;
   a manually insertable flexible prod for insertion into the loading chambers to advance the pellets from the pellet loading chambers and into the hollow central chamber; and
   wherein the central chamber further includes a locking mechanism for permanently locking the stylet end of the plunger assembly within the central chamber after the stylet end of the plunger assembly is fully retracted into the central chamber.

22. The implant device according to claim 21, wherein a plurality of deformable 'O' rings are disposed within the loading chambers to finally prevent a pellet from prematurely entering the central hollow chamber.

23. The implant device according to claim 21, wherein at least one deformable O ring is disposed at an inlet end of the loading chamber and at least one deformable O ring is disposed at an outlet end of the loading chamber.

24. The implant device according to claim 23, wherein a manually insertable removable stopper is fitted on the inlet end of each of the loading chambers.

\* \* \* \* \*